United States Patent [19]

Koulbanis et al.

[11] 4,422,952

[45] Dec. 27, 1983

[54] EMULSIONS OF THE WATER-IN-OIL TYPE USEABLE AS COSMETIC SUPPORTS OR PHARMACEUTICAL EXCIPIENTS

[75] Inventors: Constantin Koulbanis, Paris; Jean-Claude Ser, Beynes; Quang L. N'Guyen, Antony, all of France

[73] Assignee: L'Oreal, Paris, France

[21] Appl. No.: 172,825

[22] Filed: Jul. 28, 1980

[30] Foreign Application Priority Data

Aug. 2, 1979 [FR] France ............................. 79 19841

[51] Int. Cl.$^3$ .................... B01J 13/00; C09F 5/08; A61K 7/42; A61K 7/021

[52] U.S. Cl. .................................. 252/309; 252/308; 252/356; 424/59; 424/63; 424/168; 424/172; 424/289; 424/358; 424/365; 260/410.6

[58] Field of Search ............... 424/289, 63, 168, 172; 260/410.6; 252/308, 309

[56] References Cited

U.S. PATENT DOCUMENTS

| | | | |
|---|---|---|---|
| 2,733,252 | 1/1956 | Thompson et al. | 260/410.9 |
| 3,472,940 | 10/1969 | Osipow et al. | 424/365 |
| 3,846,556 | 11/1974 | Villa et al. | 424/364 |
| 4,089,954 | 5/1978 | Morelle et al. | 424/289 |
| 4,109,010 | 8/1978 | Sias | 424/289 |
| 4,184,978 | 1/1980 | France et al. | 252/309 |

FOREIGN PATENT DOCUMENTS

| | | | |
|---|---|---|---|
| 1002256 | 12/1976 | Canada. | |
| 954462 | 11/1956 | Fed. Rep. of Germany | 424/289 |
| 1955764 | 3/1971 | Fed. Rep. of Germany | 260/410.6 |
| 2293924 | 7/1976 | France | 424/289 |

OTHER PUBLICATIONS

Chemical Abstract, vol. 89, No. 14, 1978.
Chemical Abstracts, vol. 84, No. 4, 1976.

*Primary Examiner*—Dale R. Ore
*Attorney, Agent, or Firm*—Parkhurst & Oliff

[57] ABSTRACT

Emulsions of the water-in-oil type having a water phase, an oil phase and an emulsifying agent consisting of a metal or alkaline-earth metal lanolinyl lactylate. The emulsions may also be in the form of cosmetic compositions, including other cosmetic additives, or may be used as pharmaceutical excipients.

8 Claims, No Drawings

EMULSIONS OF THE WATER-IN-OIL TYPE USEABLE AS COSMETIC SUPPORTS OR PHARMACEUTICAL EXCIPIENTS

The present invention concerns the field of emulsions, notably of emulsions of the water-in-oil type, useable as cosmetic supports or pharmaceutical excipients.

Up to now and in certain cases the obtention of good water-in-oil type emulsions having good stability with time was not resolved in satisfactory manner.

In effect, it was established that certain emulsifying agents, which to permit the conferring of excellent properties to emulsions such as good oiliness and good spreading, nevertheless did not permit them to be conductive to sufficient stability, causing certain crystallization phemonena to occur during storage.

That is the case particularly with the acyl lactylates of alkaline metals or alkaline earths metals and notably of the capryl, lauroyl, stearoyl and isostearoyl lactylates of sodium, calcium, and magnesium, which have been proven to provide excellent emulsifying properties and which are widely used to obtain emulsions of the water-in-oil type or oil-in-water type, but which present the major drawback of causing, after variable storage times, a more or less abundant crystallization, which to be sure poses serious problems where one is to proceed to stock such emulsions for long periods.

In order to remedy in part these drawbacks, it has already been proposed to use in U.S. Pat. No. 3,846,556 as an emulsifying agent other types of salts of fatty acids, and more particularly metal or alkaline-earth metal lanolates, but these must be associated with hydrogenated lanolin and/or with lanolin alcohol within well determined proportions.

It has been noticed that these crystalization phenomena which can occur more less rapidly according to the storage conditions, are able to be avoided without impairing the properties of water-in-oil type emulsions, using as an emulsifying agent a metal or alkaline-earth metal lanolinyl lactylate such as the lanolinyl lactylates of magnesium, zinc, calcium or aluminium.

It has in effect been able to establish by a number of compartive analyses that, contrary to the acyl lactylates of the prior art such as the capryl, lauroyl, stearoyl and isostearoyl lactylates, the lanolinyl lactylates do not give rise to crystalization phenomena even after prolonged storage periods, particularly at relatively low temperatures, i.e., ≦15° C.

Moreover, in comparison with metal or alkaline earth metal lanolates, it has been established that to avoid the phenomena of crystalization and to obtain excellent emulsions, it was not absolutely necessary to associate therewith a co-emulsifier such as hydrogenated lanolin and/or lanolin alcohol.

The use in emulsions according to the invention of a metal or alkaline-earth metal lanolinyl lactylates, and in particular the use of magnesium, zinc, calcium or aluminium lanolinyl lactylates permits thus to obtain emulsions of better qualities, in a more simple way and at low cost due to the fact that the use of a co-emulsifier is not a necessity.

The present invention accordingly provides, an emulsion of the water-in-oil type, comprising a water phase, an oil phase and an emulsifying agent, said emulsifying agent being selected from the group consisting of the metal or alkaline-earth metal lanolinyl lactylates, and more particularly the lanolinyl lactylates of magnesium, zinc, calcium and aluminium.

The lanolinyl lactylates used according to the invention, can be represented by the following general formula:

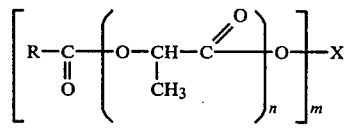

wherein:

R represents the hydrocarbon radical of lanolic acid which is a mixture of aliphatic radicals substituted or not and eventually hydroxylated;

X is Mg, Zn, Ca or Al;

n is in the range between 0.5 and 6 and is preferably between 0.8 and 2, indicating a mean number of lactyl groups;

and m is 2 when X is Mg, Zn or Ca, or 3 when X is Al.

The lanolinyl lactylic acid, as well as the salts of magnesium, zinc, calcium and aluminium can be obtained with good yields according to the procedure described in U.S. Pat. No. 2,733,252.

In particular, one uses the method consisting of esterifying lanolic acid with lactylic acid under alkaline conditions in the presence of ions of an alkali metal or alkaline-earth metal, present in the form of hydroxides, oxides, carbonates bicarbonates or of a cationic salt of a weak and volatile acid in an amount greater than the catalytic amount (of the order of 0.3 to 1.2 equivalent of metal per equivalent of lanolic acid).

It is preferable to react the lanolic acid with about 1.5 to 4 equivalents by weight of lactic acid at a temperature of about 150°–210° C. under an atmosphere of nitrogen.

Free lanolinyl-lactylic acid can be obtained by acidification of the reaction mixture with a strong acid such as for example sulfuric acid. After the acidification and water removing the acid is dried under vacuum at a temperature of about 100° to 150° C.

As lanolic acid one preferably uses those sold under the commercial names of AMERLATE WFA, sold by Amerchol (American Cholesterol Products, Inc., Edison, N.J.); LANACID, sold by Matrom; and Lanolic Acids, sold by Croda. The mean weight of the lanolic acid is generally comprised between 350 and 480.

Starting from the lanolinyl lactylic acid, the preparation of lanolinyl lactylates can be carried out by two different methods:

either by double decomposition, which method consists first to obtain the sodium salt or potassium salt at a dilution such that it is in isotropic solution and then precipitating from that solution the salt of the desired lanolinyl lactylic acid by addition of a solution of mineral salt, preferably of a chloride, or by direct action of a metal or alkaline-earth metal hydroxide on the lanolinyl lactylic acid.

According to the invention, the lanolinyl lactylates should preferably not contain (as an impurity) more than 5% by weight of lanolinyl lactylic acid.

The concentration of the emulsifying agent in the emulsions according to the invention is generally comprised between 5 and 20% and preferably between 6 and 12% by weight based on the total weight of the emulsion.

As previously indicated herein, it is not necessary to utilize a co-emulsifier in order to obtain, on one hand, good stability and on the other hand good emulsifying properties; however it is may be useful in order to obtain a weak viscosity to make use of the hydrogenated lanolin in a ratio of about 4 to 12% and preferably of 6 to 8% by weight based on the total weight of the emulsion.

As hydrogenated lanolins one preferably uses in this case those known under the commercial names; HYDROLAN, having a melting point of 48°-53° C., sold by Millmaster Onyx; HYDROXYOL, sold by Malstrom; and SUPER-SAT, having a melting point of 48°-50° C., sold by Rita Chemical.

According to the invention the water phase of the emulsions is present in an amount from about 20 to 75% by weight and preferably from 25 to 60% by weight, and the oil phase is present in an amount from 20 to 75% by weight and preferably from 30 to 55% by weight based on the total weight of the emulsion.

A large variety of products can be employed to form the oil phase of the emulsion such as:

animal oils such as horse oil or pork oil;

vegtable oils such as sweet almond oil, avocado oil, castor oil, olive oil, raisin seed oil, poppy oil, rape oil, peanut oil, corn oil, hazel nut oil, jojoba oil, safflower oil, and wheat germ oil;

hydrocarbonated oils such as paraffin oil, Purcellin oil, the perhydrosqualene (shark oil) and solutions of microcrystalline wax in the oils, mineral oils and more particularly oils whose initial distillation point at atmospheric pressure is about 250° C. and whose final distillation point is of the order of 410° C.

One can also use certain synthetic products such as for example saturated esters and notably isopropyl palmitate, isopropyl myristate, butyl myristate and cetyl myristate, hexadecyl stearate, ethyl palmitate, as also the triglycerides of octanoic acids and decanoic acids and cetyl ricinoleate.

The oil phase of the emulsions may also contain certain waxes, and notably Carnauba wax, beeswax, and ozokerite wax or Candellila wax.

Preferably, the oil phase of the emulsions has a dielectric constant comprised between 1.8 and 4.5 and more preferably between 2 and 3.1.

These cosmetic products may be presented in the form of moisturizing creams, such as for example sun creams, face creams, body creams or hands creams or in the form of moisturizing rouges of make-up foundations.

When the water-in-oil emulsions according to the invention are presented in the form of cosmetic products, they contain various other ingredients which are generally present in such compositions, and in particular preservative agents, perfumes, dyestuffs, solar filters, pigments and the like.

According to another embodiment, the emulsions according to the invention can also be used as excipients for diverse pharmaceutical products, such as creams, balms, ointments, and the like.

The following Examples further illustrate the present invention:

EXAMPLE I

One prepares according to the invention a water-in-oil emulsion which can be used as a cosmetic support or pharmaceutical excipient by proceeding to mix the following ingredients:

| Calcium lanolinyl lactylate | 8 g |
|---|---|
| Vaseline | 10 g |
| Paraffin oil | 25 g |
| Preservative (methyl parahydroxybenzoate) | 0.3 g |
| Perfume | 0.5 g |
| Demineralized water g.s.p. | 100 g |

EXAMPLE II

One prepares according to the invention a water-in-oil emulsion which can be used as a cosmetic support or pharmaceutical excipient by proceeding to mix the following ingredients:

| Magnesium Lanolinyl lactylate | 3.3 g |
|---|---|
| Hydrogenated lanolin | 2.7 g |
| Vaseline | 15 g |
| Paraffin oil | 18 g |
| Perfume | 0.4 g |
| Demineralized water g.s.p. | 100 g |

EXAMPLE III

One prepares according to the invention a water-in-oil emulsion which can be used as a cosmetic support or pharmaceutical excipient by proceeding to mix the following ingredients:

| Zinc lanolinyl lactylate | 12 g |
|---|---|
| Vaseline | 15 g |
| Paraffin oil | 23 g |
| Perfume | 0.6 g |
| Preservative | 0.25 g |
| Demineralized water | 100 g |

The water-in-oil emulsions according to the preceding examples are fine and particularly agreeable to touch when they are spread on the skin. Tests of storage and stability with time (1 to 3 months) and at temperatures of −15° C. to +40° C. do not permit to notice instability phenomena of the emulsions and the presence of crystals.

EXAMPLE IV

One prepares according to the invention a water-in-oil emulsion in the form of a sun cream by proceeding to mix the following ingredients:

| Magnesium lanolinyl lactylate | 9 g |
|---|---|
| Vaseline | 12 g |
| Paraffin oil | 5 g |
| Isopropyl myristate | 14 g |
| Benzylidene camphor | 3 g |
| Parahydroxy propyl benzoate | 0.35 g |
| Perfume | 0.35 g |
| Sterile demineralized water g.s.p. | 100 g |

EXAMPLE V

One prepares according to the invention a water-in-oil emulsion in the form of a make-up foundation by proceeding to mix the following ingredients:

| | |
|---|---|
| Calcium lanolinyl lactylate | 12 g |
| Cetyl laurate | 5 g |
| Sweet almond oil | 3 g |
| Vaseline | 15 g |
| Paraffin oil | 15 g |
| Red iron oxide | 0.7 g |
| Yellow iron oxide | 0.9 g |
| Titanium oxide | 2 g |
| Sodium merthiolate | 0.005 g |
| Perfume | 0.25 g |
| Sterile demineralized water g.s.p. | 100 g |

EXAMPLE VI

One prepares according to the invention a water-in-oil emulsion in the form of a moisturizing rouges by proceeding to mix the following ingredients:

| | |
|---|---|
| Zinc lanolinyl lactylate | 7 g |
| Hydrogenated lanolin | 5 g |
| Perhydrosqualene | 15 g |
| Purcellin oil | 8 g |
| Vaseline | 10 g |
| Titanium oxide | 1.5 g |
| Black iron oxide | 0.1 g |
| D and C Red No. 8 colorant | 0.95 g |
| Parahydroxy methyl benzoate | 0.15 g |
| Parahydroxy propyl benzoate | 0.2 g |
| Perfume | 1 g |
| Sterile demineralized water g.s.p. | 100 g |

The lanolinyl lactylates used in the water-in-oil emulsions according to the invention have been prepared-/and supplied by Societe GRINSTED Products.

What is claimed is:

1. A water-in-oil emulsion comprising 20 to 75% by weight of a water phase, 20 to 75% by weight of an oil phase and as an emulsifying agent 5 to 20% by weight of a metal lanolinyl lactylate selected from the group consisting of magnesium, zinc, calcium and aluminum lanolinyl lactylate.

2. An emulsion as claimed in claim 1, wherein said agent is about 6 to 12% by weight of said emulsion.

3. An emulsion as claimed in claim 1, wherein said water phase is about 25 to 60% by weight of said emulsion.

4. An emulsion as claimed in claim 1, wherein said oil phase is about 30 to 55% by weight of said emulsion.

5. An emulsion as claimed in claim 1, wherein said oil phase has a dielectric constant between 1.8 and 4.5.

6. An emulsion as claimed in claim 5, wherein said dielectric constant is between 2.0 and 3.1.

7. An emulsion as claimed in claim 1, further comprising a hydrogenated lanolin co-emulsifier which is about 4 to 12% by weight of said emulsion.

8. An emulsion as claimed in claim 7, wherein said co-emulsifier is from 6 to 8% by weight of said emulsion.

* * * * *